US009102576B1

(12) United States Patent
Spowart et al.

(10) Patent No.: US 9,102,576 B1
(45) Date of Patent: Aug. 11, 2015

(54) PARTICULATE-BASED REACTIVE NANOCOMPOSITES AND METHODS OF MAKING AND USING THE SAME

(71) Applicant: The United States of America, as represented by the Secretary of the Air Force, Washington, DC (US)

(72) Inventors: Jonathan E. Spowart, Dayton, OH (US); Christopher A. Crouse, Valparaiso, FL (US); Christian J. Pierce, Alamogordo, NM (US); Breanna K. Hardenstein, Lafayette, IN (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 382 days.

(21) Appl. No.: 13/795,800

(22) Filed: Mar. 12, 2013

Related U.S. Application Data

(60) Provisional application No. 61/653,486, filed on May 31, 2012.

(51) Int. Cl.
| | |
|---|---|
| *B82Y 5/00* | (2011.01) |
| *B32B 5/16* | (2006.01) |
| *B05D 3/00* | (2006.01) |
| *C08F 2/44* | (2006.01) |
| *C06B 43/00* | (2006.01) |
| *C06B 45/00* | (2006.01) |

(52) U.S. Cl.
CPC . *C06B 43/00* (2013.01); *B05D 3/00* (2013.01); *B32B 5/16* (2013.01); *B82Y 5/00* (2013.01); *C06B 45/00* (2013.01); *C08F 2/44* (2013.01)

(58) Field of Classification Search
CPC ............... C08F 2/44; B32B 5/16; B05D 3/00; B82Y 5/00
USPC ........... 524/413; 428/407; 427/331; 977/773, 977/774, 890
See application file for complete search history.

(56) References Cited

U.S. PATENT DOCUMENTS

| | | | |
|---|---|---|---|
| 6,057,488 A | 5/2000 | Koper et al. | |
| 6,353,037 B1 | 3/2002 | Thunhorst et al. | |
| 6,417,423 B1 | 7/2002 | Koper et al. | |
| 6,676,727 B2 | 1/2004 | Pozarnsky | |
| 6,682,584 B2 | 1/2004 | Pozarnsky et al. | |
| 6,688,494 B2 | 2/2004 | Pozarnsky et al. | |
| 6,689,190 B2 | 2/2004 | Pozarnsky | |
| 6,962,634 B2 | 11/2005 | Nielson et al. | |
| 7,217,754 B2 | 5/2007 | Koloski et al. | |
| 7,279,129 B2 | 10/2007 | Lanz et al. | |
| 7,307,117 B2 | 12/2007 | Nielson et al. | |
| 7,338,711 B1 | 3/2008 | Brousseau, III | |
| 7,455,886 B2 | 11/2008 | Rao et al. | |
| 7,568,432 B1 | 8/2009 | Baker et al. | |
| 7,614,348 B2 | 11/2009 | Truitt et al. | |
| 7,886,668 B2 | 2/2011 | Hugus et al. | |
| 7,927,437 B2 | 4/2011 | Gangopadhyay et al. | |
| 8,372,908 B2 | 2/2013 | Guo et al. | |
| 2007/0272112 A1 | 11/2007 | Nielson et al. | |
| 2010/0240804 A1 | 9/2010 | Irwin et al. | |
| 2011/0105643 A1 | 5/2011 | Chun et al. | |
| 2011/0159291 A1 | 6/2011 | Sun et al. | |
| 2012/0024180 A1 | 2/2012 | Waddell et al. | |
| 2012/0064140 A1 | 3/2012 | Qian et al. | |

OTHER PUBLICATIONS

Mahdavian et al. "Nanocomposite particles with core-shell morphology III: preparation and characterization of nano Al2O3-poly(styrene-methyl methacrylate) particles via miniemulsion polymerization", Polym. Bull. (2009), vol. 63, pp. 329-340.*
Guo et al. "Surface functionalized alumina nanoparticle filled polymeric nanocomposites with enhanced mechanical properties", J. Mater. Chem., 2006, 16, pp. 2800-2808.*
Osso, D., et al, "Synthesis of Alumina-Metal Nanocomposites by Mechanical Alloying," Journal de Physique IV, C7, Supplement III, vol. 3 (1993) pp. 1407-1412.
Guo, Zhanhu, et al, "Surface functionalized alumina nanoparticle filled polymeric nanocomposites with enhanced mechanical properties," J. Mater. Chem. (2006) 16, pp. 2800-2808.
Mahdavian, Ali Reza, et al., "Nanocomposite particles with core-shell morphology III: preparation and characterization of nano Al2O3-poly(styrene-methyl methacrylate) particles via miniemulsion polymerization," Polym. Bull. (2009) 63:329-340.
Sun, Haizhu, et al., "In situ preparation of Nanoparticles/polymer composites," Sci China Ser E-Tech Sci, 2008, vol. 51, No. 11,1886-1901.
Jeon, In-Yup, et al., "Nanocomposites Derived from Polymers and Inorganic Nanoparticles," Materials 2010,3, 3654-3674; doi:10.3390/ma3063654.
Zuev, Vjacheslav V., et al., "Fullerene C60 as stabiliser for acrylic polymers," Polymer Degradation and Stability 90 (2005) 28-33.
Risha, G.A., et al., "Combustion of Nano-Aluminum and Liquid Water," Proceedings of the Combustion Institute 31 (2007) 2029-2036.
Levitas, Valery I., et al "Melt dispersion mechanism for fast reaction of nanothermites," Applied Physics Letters 89, 071909, 2006.

(Continued)

*Primary Examiner* — Michael M Bernshteyn
(74) *Attorney, Agent, or Firm* — AFMCLO/JAZ; Chastity Whitaker

(57) ABSTRACT

Reactive nanocomposites, foams, and structures comprising functionalized metal nanoparticles that are incorporated into a fluorinated polymer matrix using an in-situ polymerization process and methods of making and using the same. The reactive nanocomposites, foams, and structures according to the present invention demonstrate enhanced mechanical properties due to the direct chemical integration of the nanometal fuel particles into the fluoropolymer matrix. In addition, the reactive nanocomposites, foams, and structures may be processed using conventional polymer processing and may be used to fabricate materials such as reactive liners, casings, and other components and inserts. The intense heat produced during reaction may further be used in a variety of applications such as disinfection, decontamination, and/or destruction.

21 Claims, 10 Drawing Sheets

(56) References Cited

OTHER PUBLICATIONS

Watson, Kyle W., et al., "Fast reactions with nano- and micrometer aluminum: A study on oxidation versus fluorination," Combustion and Flame 155 (2008) 619-634.

Crouse, Christopher A., et al., "Influencing solvent miscibility and aqueous stability of oxide passivated aluminum nanoparticles through surface functionalization with acrylic monomers," ACS Appl. Mater. Interfaces, 2010, 2 (9), pp. 2560-2569.

Hunt, E.M., et al., "Combustion synthesis of metallic foams from nanocomposite reactants," Intermetallics 14 (2006) 620-629.

* cited by examiner

PARTICULATE-BASED REACTIVE NANOCOMPOSITES AND METHODS OF MAKING AND USING THE SAME

CROSS-REFERENCE TO RELATED APPLICATIONS

This application claims the benefit of U.S. Provisional Patent Application No. 61/653,486, filed on May 31, 2012, by Spowart, et al., entitled "Particulate-Based Reactive Nanocomposites and Methods of Making and Using the Same," which is herein incorporated by reference in its entirety.

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

This invention relates generally to the field of reactive composites comprising nanoparticles. More particularly, it relates to fluorinated acrylic reactive nanocomposites and methods of making and using the same.

2. Description of the Related Art

Reactive nanocomposites combine the high reaction rates of molecular explosives and materials with the high energy density of composite materials. A reactive nanoparticle composite (nanocomposite) typically comprises a fuel such as reactive metal nanoparticles incorporated into a polymer matrix, which acts as an oxidizer. Reactive metal nanoparticles typically include Al, B, Mg, Si, Zr, Hf, Fe, and Ti or alloys or mixtures thereof. To achieve the enhanced reaction rates and mechanical properties typically observed for reactive nanocomposites, the metal nanoparticle should be distributed evenly throughout the polymer matrix, and a variety of methods exist to combine the metal nanoparticles and the polymer matrix. One common method includes powder compaction, which involves sonochemical mixing of the metal nanoparticles with the polymer powder(s) in a solvent, followed by evaporation of the solvent and mechanical compression of the mixed powders into pellet form. Other common methods include melt blending and solution mixing.

However, these methods share a number of limitations and drawbacks. The resulting nanocomposites generally possess minimal chemical and/or physical interaction between the individual component particles (polymer-metal and polymer-polymer), and the metal nanoparticles are often unevenly distributed throughout the polymer matrix. Both of these problems may lead to a nanocomposite that fails to achieve adequate mechanical properties for many practical applications. To obtain better bonding between the individual components, a binder material may be added, but due to the high specific surface area of nanoparticles, a significant amount of binder is often required. The binder may then interfere with the material properties and performance of the composite material. Additional processing steps such as sintering or extrusion may also be performed. However, sintering is often performed at elevated temperatures that are near the temperature required to initiate pre-ignition reactions in the nanocomposite. In addition, processing of some polymers by extrusion requires additional chemicals and/or solvents that may affect the mechanical properties of the reactive nanocomposite. Various in-situ polymerization techniques have been developed to improve distribution of the metal nanoparticles in the polymer matrix and to improve interaction between the nanoparticle and the polymer.

Polytetrafluoroethylene (PTFE) is one of the most common fluorinated polymers used in nano-metal/polymer nanocomposite reactive systems. PTFE has a fully fluorinated carbon backbone, resulting in a fluorine density of 75% by weight, higher than any other fluorinated polymer system. Additionally, PTFE is available in both micron- and nano-scale powders that are amenable to mixing with many metal nanoparticles. However, PTFE is generally not compatible with in-situ polymerization techniques. Suspension or dispersion polymerizations are commonly used to prepare high quality PTFE, but these approaches require the use of both an aqueous layer and elevated temperatures, which limits the polymer's compatibility with many reactive metals like aluminum that react with water, especially at elevated temperatures. In addition, processing of PTFE by extrusion requires the addition of other chemicals and/or solvents or modification of the polymer backbone to yield a co-polymer. This step adds considerable cost to the material and makes it less attractive to the end user.

SUMMARY OF THE INVENTION

The present invention includes reactive nanocomposites and methods of making and using the same. The reactive nanocomposites may comprise functionalized reactive nanoparticles that are incorporated into a polymeric matrix using an in-situ polymerization process. The in-situ polymerization process creates a nanocomposite that demonstrates increased amounts of bonding at the polymer-particle interface, which results in enhanced mechanical properties, including increased load-bearing capacity. The reaction rate and extent of the reactive nanocomposites may also be finely tuned by altering the microstructure and chemical composition of the material, including the amount and particle size distribution of the nanoparticles and the makeup of the polymer matrix.

The present invention includes a method of making a reactive nanocomposite comprising the steps of: dissolving a ligand in a solvent; adding the ligand to a mixture comprising a plurality of reactive metal nanoparticles and a free radical scavenger; stirring the mixture and the ligand at a first elevated temperature to produce functionalized reactive metal nanoparticles; and mixing the functionalized reactive metal nanoparticles with a free-radical initiator, at least one fluorinated monomer, and additional solvent at a second elevated temperature, in which the ligand is capable of interacting with the fluorinated monomer and with an exterior surface of the reactive metal nanoparticles such that the functionalized metal nanoparticles are incorporated into a fluorinated polymer matrix by in-situ polymerization to form the reactive nanocomposite.

In one embodiment, the reactive metal nanoparticle comprises at least one of Al, B, Mg, Si, Zr, Hf, Fe, and Ti, and alloys or mixtures thereof. In another embodiment, the ligand comprises at least one of (3-methacryloxypropyl)trimethoxysilane, 2-carboxyethylacrylate, and phosphoric acid 2-hydroxyethyl methacrylate ester. In another embodiment, the fluorinated polymer matrix comprises at least one fluorinated acrylate polymer. In an additional embodiment, the fluorinated polymer matrix comprises at least one of poly(1H,1H,2H,2H-perfluorodecyl methacrylate), poly(vinylidene fluoride), and poly(hexafluoropropylene-co-vinylidene fluoride).

In a further embodiment, the method further comprises milling the reactive nanocomposite to form a reactive powder having a desired particle size. In another embodiment, the method further comprises incorporating a plurality of additional oxidizer particles into the reactive nanocomposite, in which the additional oxidizer particles comprise at least one of a second reactive metal particle, a metal oxide, a complex inorganic oxide, and a polyoxometallate. In yet another embodiment, the method further comprises incorporating at least one of a silver salt, an iodine salt, and a quaternary ammonium salt into the reactive nanocomposite. In an additional embodiment, the method further comprises incorporating at least one energetic material into the reactive nanocomposite. In one embodiment, incorporating the energetic material into the reactive nanocomposite further comprises forming a reactive laminate comprising at least one layer comprising the reactive nanocomposite and at least one layer comprising the energetic material.

In an alternative embodiment, the method further comprises enclosing the reactive nanocomposite in an external structural shell, wherein the external structural shell comprises at least one of a glass fiber composite, a carbon fiber composite, an aramid composite, a monolithic metal, a metal laminate, and a structural polymeric matrix. In a further embodiment, the method further comprises combining the reactive nanocomposite with at least one of a thermosetting polymer matrix and a thermoplastic polymer matrix.

The present invention further includes methods of using a reactive nanocomposite made according to a presently disclosed method. In one embodiment, the method of use comprises forming the reactive nanocomposite into a reactive nanocomposite structure having a desired structure shape, wherein the reactive nanocomposite structure comprises at least one of a liner, a coating, a casing, a sleeve, an insert, a cylinder, a shape charge, a rod, and an open cell foam. In one embodiment, the method further comprises filling the reactive nanocomposite structure with at least one of an explosive material, a pyrotechnic material, a pyrophoric material, a blast-enhancing material, a fragmentation-enhancing material, and a mechanical shear-inducing material.

In another embodiment, the method of use further includes using a reactive nanocomposite in a printing process. One embodiment of the method comprises the steps of: modifying the reactive nanocomposite to form a reactive nanocomposite fluid, in which modifying the reactive nanocomposite comprises at least one of suspending the reactive nanocomposite in a carrier liquid, dissolving the reactive nanocomposite in a solvent, and heating above a melting point of the reactive nanocomposite; depositing at least one layer of the reactive nanocomposite fluid onto a substrate surface; and forming at least one of a desired shape or a desired pattern comprising the reactive nanocomposite, in which the desired shape or desired pattern is formed upon at least one of evaporation of the carrier liquid, evaporation of the solvent, and cooling below the melting point of the reactive nanocomposite. In one embodiment, the reactive nanocomposite fluid further comprises at least one of a pigment or dye. In another embodiment, depositing the reactive nanocomposite comprises three-dimensional printing. In a further embodiment, the method further comprises depositing a plurality of layers of the reactive nanocomposite fluid onto the surface of the substrate to create a reactive liner.

The present invention further includes a method of making a reactive nanocomposite foam comprising the steps of: providing a reactive nanocomposite made according to the present invention; providing an open cell foam defining a core and a plurality of pores; placing the open cell foam into a device having a desired final shape; and extruding the reactive nanocomposite into the device such that the reactive nanocomposite infiltrates the open cell foam to fill at least a portion of the pores to form the reactive nanocomposite foam. In one embodiment, the method further comprises filling the core of the open cell foam with at least one of an explosive material, a pyrotechnic material, a pyrophoric material, a blast-enhancing material, a fragmentation-enhancing material, and a mechanical shear-inducing material.

The present invention further includes a method of using a reactive nanocomposite foam made according to a presently disclosed method. In one embodiment, the method comprises forming the reactive nanocomposite foam into a reactive nanocomposite foam structure, wherein the reactive nanocomposite foam structure comprises at least one of a liner, a coating, a casing, a sleeve, an insert, a cylinder, a shape charge, a rod, and a foam. In another embodiment, the method further comprises filling the reactive nanocomposite foam structure with at least one of an explosive material, a pyrotechnic material, a pyrophoric material, a blast-enhancing material, a fragmentation-enhancing material, and a mechanical shear-inducing material.

DETAILED DESCRIPTION OF THE INVENTION

Figure 1:
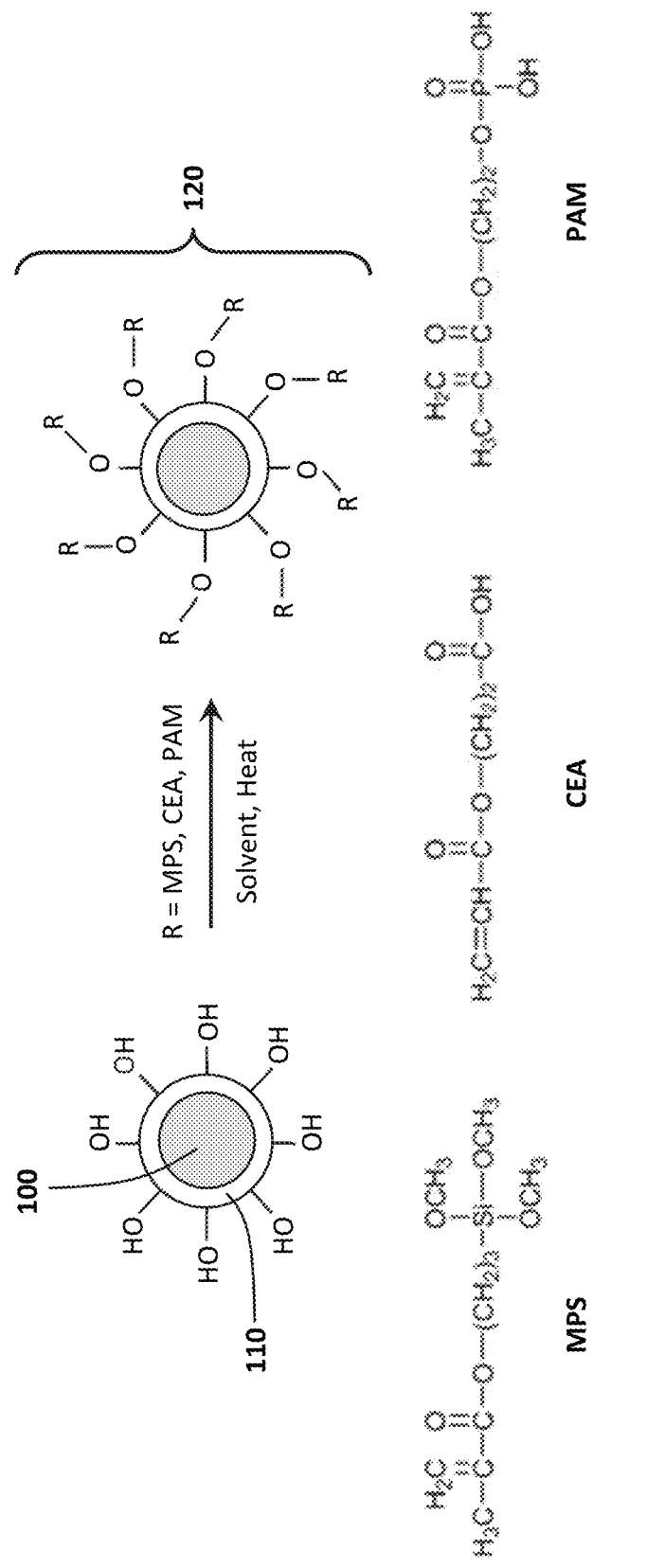
FIG. 1 a diagram of the synthesis of an exemplary method of forming a functionalized metal nanoparticle.

The present invention includes reactive nanocomposites and methods of making and using the same. The reactive nanocomposites comprise functionalized reactive nanoparticles that are incorporated into a polymeric matrix using an in-situ polymerization process. The fuel for the reactive nanocomposite generally comprises one or more types of metal nanoparticles, which is used generally throughout to refer to micron-($\geq$1 micron), sub-micron-(200 nm-1 micron), or nanometer-sized (<200 nm) particles. The metal nanoparticles may comprise various morphologies such as flakes, spheres, rods, clusters, aggregates, and milled or mechanically alloyed particles and may comprise, but are not limited to, Al, B, Mg, Si, Zr, Hf, Fe, and Ti, and alloys or mixtures thereof.

The exterior surface of the metal nanoparticles is coated or functionalized with a ligand, which may comprise any monomer, polymer, molecule, or other chemical moiety with suitable functionality that is capable of interacting with both the metal nanoparticle and the monomers comprising the polymer matrix. One or more ligands may be dissolved in a solvent, and the resulting solution may be mixed with metal nanoparticles at an elevated temperature, resulting in functionalized metal nanoparticles in which the ligand interacts with and coats and/or encapsulates the exterior surface of the metal nanoparticles. Where the ligand is a monomer or polymer, an optional free radical scavenger may be used to prevent unwanted polymerization of the ligand during functionalization. Exemplary ligands may include, but are not limited to, acrylic monomers such as (3-methacryloxypropyl)trimethoxysilane (MPS); 2-carboxyethylacrylate (CEA); or phosphoric acid 2-hydroxyethyl methacrylate ester (PAM).

The functionalized nanoparticles are then incorporated into a polymeric matrix via in-situ polymerization. The functionalized metal nanoparticles are mixed, at an elevated temperature, with one or more types of fluorinated monomers and a free-radical initiator. The ligand interacts with the monomers and allows the functionalized nanoparticles to be chemically incorporated into the polymer matrix. For example, where the ligand is a monomer such as MPS, CEA, or PAM, the ligand copolymerizes with the fluorinated monomers. The polymer matrix may provide mechanical strength to the composite material. In one embodiment, the polymeric matrix may be a fluorinated homopolymer or copolymer, and in another embodiment, the polymer matrix comprises a polymer having a fluorine balance equivalent to 60.7% by mass. The polymer may comprise a fluorinated acrylate or methacrylate homopolymer or copolymer comprising the monomer 1H,1H,2H,2H-perfluorodecyl methacrylate (PFDMA), as well as other melt-processable fluoropolymers including, but not limited to, poly(vinylidene fluoride) (PVDF) and poly (hexafluoropropylene-co-vinylidene fluoride). The fluoropolymer matrix may also be substituted for any combination of copolymer system that is perfluorinated or fully or partially fluorinated.

Fluorinated polymers such as poly(tetrafluoroethylene) (PTFE) and its co-polymers, fluorinated elastomers, and molecular fluorocarbons have been shown to be suitable oxidizer materials for metal nanoparticles such as nano-aluminum ("nano-Al"). The stoichiometric reaction of Al with a pure fluorocarbon (e.g. PTFE; $\Delta H_F = -809.60$ kJ/mol) yields elemental carbon and aluminum trifluoride as shown in Equation 1.

$$2Al + 3(-CF_2-)_n \rightarrow 3C + 2AlF_3 \quad \Delta H^0 = -591.98 \text{ kJ} \quad (1)$$

Formation of $AlF_3$ ($\Delta H_F$ ($AlF_3$)=−1510.39 kJ/mol) yields −56.10 kJ/gram of Al, which is nearly twice the energy liberated by reacting Al with oxygen to yield $Al_2O_3$ ($\Delta H_F$ ($Al_2O_3$)=−1675.72 kJ/mol) and −30.98 kJ/gram of Al. The potential increase makes fluorinated materials viable alternatives to conventional metal oxide powders in many applications.

PFDMA is a particularly suitable fluoropolymer for use in fabricating reactive nanocomposites according to the present invention. PFDMA may be used with nano-Al because the polymer does not compromise the reactivity of nano-Al, and the PFDMA monomers may be polymerized in-situ with the functionalized nano-Al particles. In addition, PFDMA yields a polymer that is more processable than PTFE. PFDMA possesses a highly fluorinated alkyl tail, analogous to a PTFE oligomer and contains about 60% fluorine by weight. PFDMA also contains a readily polymerizable methacrylic head that is amenable to free-radical polymerization and is similar in structure to the 2-hydroxyethyl methacrylate ester used to functionalize the nano-Al. Furthermore, PFDMA is commercially available at a moderate cost and is compatible with many solvents, making it desirable for solution polymerization. Reactive nanocomposites comprising functionalized nano-Al and PFDMA are referred to throughout as aluminized fluorinated acrylic ("AlFA") nanocomposites. Various AlFA-X nanocomposites (X denotes the particle content in terms of particle wt %) may be manufactured in which $0 < X \leq 90$ wt %. In one embodiment, $20 \leq X \leq 60$.

The reactive nanocomposites according to the present invention demonstrate increased amounts of bonding at the polymer-particle interface due to the direct chemical integration of the fuel nanoparticles into the fluoropolymer matrix. Chemical integration of the nanoparticles into the fluoropolymer matrix results in a continuous phase at the particle-polymer interface and gives the reactive nanocomposites enhanced mechanical properties, including increased load-bearing capacity as compared to conventional pressed powder nanocomposites. The reaction rate and extent of the reactive nanocomposites may be finely tuned by changing the microstructure and chemistry of the material, including the amount and particle size distribution of the fuel particles. The chemical composition of the polymer may also be varied, including the amount of fluorine and other oxidizing species, as well as the presence or absence of one or more additional co-polymers.

In addition, the reactive nanocomposites exhibit thermoplastic behavior, which allows them to be processed using conventional polymer processing techniques including melt-casting, extrusion, blow-molding, vacuum molding, compression molding, stamping, resin-transfer molding, vacuum-assisted resin-transfer molding, electrospinning, melt spinning, printing, spraying, and other direct-write methods, or combinations thereof. A number of devices may be used alone or in conjunction with these polymer processing techniques to achieve the desired final shape. These devices may include, but are not limited to, a clam-shell mold, a simple cavity (with or without a mandrel), or a die. The nanocomposite may also be machined into a final product shape. These capabilities allow the reactive nanocomposites to be formed into more complex geometry articles, which may lead to more efficient component and/or munition design.

The reactive nanocomposites according to the present invention further demonstrate enhanced water and/or moist air atmospheric stability due to the hydrophobic nature of the fluoropolymer, leading to an increased shelf-life and easier materials handling. They also possess improved electrostatic discharge sensitivity over currently available nanothermite compositions, leading to increased safety factors for materials handling and reduced risk of explosion. Finally, the reactive nanocomposites are chemically compatible with many common solvents, including aircraft fuels and oils, hydrocarbons, other fluorinated systems, and other polymers such as epoxies, acrylics, polyurethanes, polyethers, and other fluoropolymers.

The presently disclosed reactive nanocomposites may be used to fabricate a variety of reactive materials including, but not limited to, munitions casings, reactive liners, shaped charges, blast enhancement materials, chemical and/or biological agent neutralization materials, or structural reactive material and components. The reactive nanocomposite may be used to fabricate materials to be used as a pyrolant for applications such as aerial decoy or signaling flares, day/night spotter rounds, and infrared (IR) emitters, and as a reactive material suitable for a parachute disreefing device. The composition of the reactive nanocomposite may also be tuned to yield a material capable of acting as a solid state and/or gelled propellant. In addition, the intense heat produced during reaction may be used to disinfect, decontaminate or otherwise affect biological processes including food preparation and cooking, or to provide a local heat source for additional chemical or physical processes such as brazing, welding, or thermoplastic bonding.

Other potential uses include applications where the reactive nanocomposites may be used as energetic materials to destroy or render useless valuable items such as would be used in an anti-theft device, for example. Because the materials do not require additional oxidizers in order to react, they are expected to provide similar functionalities under inert atmospheres, in a vacuum, in space, or underwater. Furthermore, because the reactive nanocomposites have enhanced mechanical properties as compared to conventional energetic materials, they may be effective in reducing the sensitivity of existing munitions to sympathetic detonation phenomena.

Referring to the drawings, like reference numerals may designate like or corresponding parts throughout the several views.

FIG. 1 is a diagram of an exemplary method of synthesizing a functionalized metal nanoparticle. A powder comprising metal nanoparticles 100 and hydroquinone (an optional free radical scavenger to prevent unwanted polymerization) are combined. In the embodiment depicted in FIG. 1, the metal nanoparticle 100 is nano-Al with an aluminum oxide shell 110. The metal nanoparticle 100 is functionalized with a ligand R. In the embodiment depicted in FIG. 1, the ligand R is a molecule and may include (3-methacryloxypropyl) trimethoxysilane (MPS); 2-carboxyethylacrylate (CEA); or phosphoric acid 2-hydroxyethyl methacrylate ester (PAM). The ligand R is dissolved in a solvent such as cyclohexanone and added to the metal nanoparticles 100 and hydroquinone (if used). The mixture is heated in a nitrogen atmosphere, resulting in functionalized metal nanoparticles 120. The functionalized metal nanoparticles 120 are then are isolated by vacuum filtration, followed by washing and drying.

Figure 2:
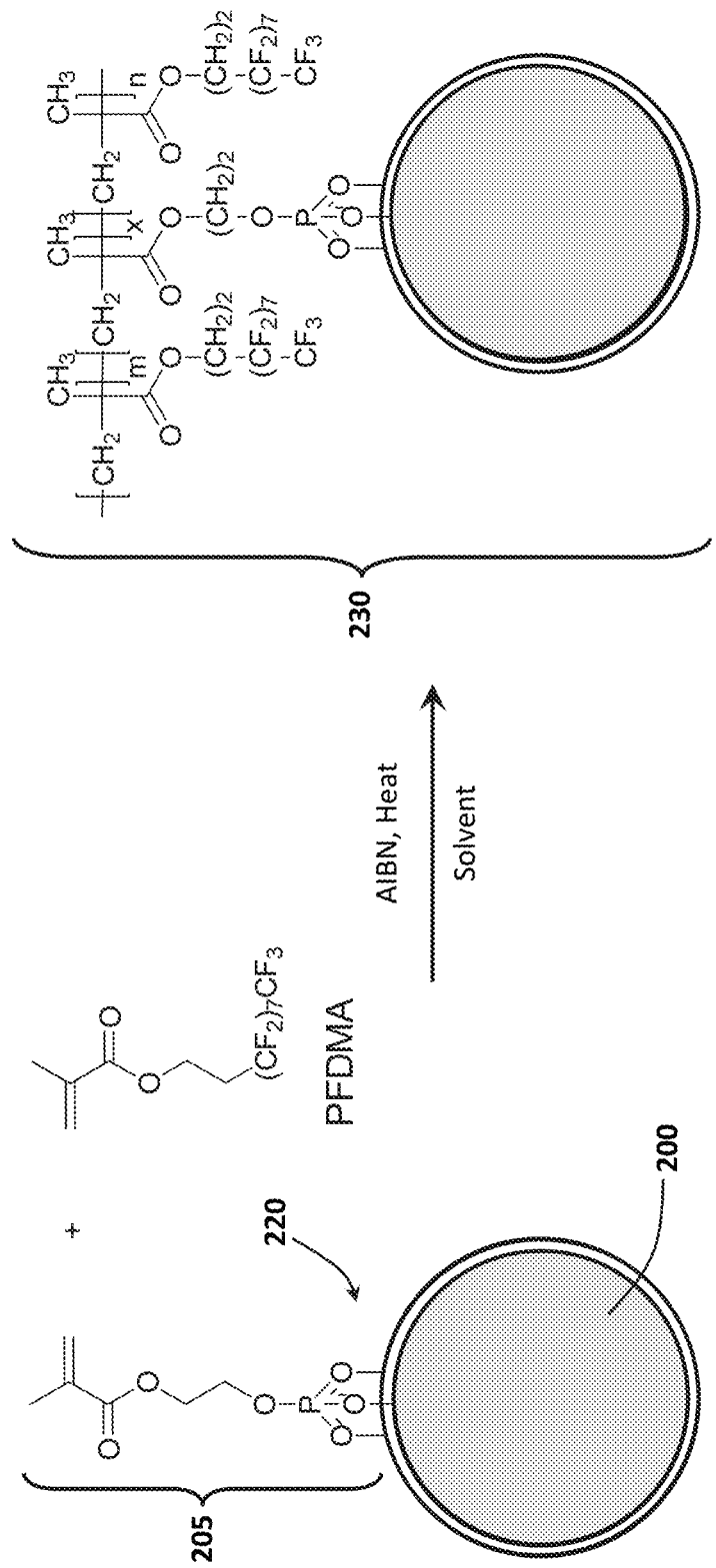
FIG. 2 is a diagram of the synthesis of an exemplary reactive nanocomposite using an in-situ polymerization process.

FIG. 2 is a diagram of the synthesis of an exemplary AlFA nanocomposite made according to the present invention using an in-situ polymerization process. A metal nanoparticle 200 is functionalized with a ligand 205 substantially as shown in FIG. 1 to generate a functionalized metal nanoparticle 220. In the embodiment depicted in FIG. 2, the metal nanoparticle 200 is aluminum, and the ligand 205 is PAM. Other ligands such as MPS and/or CEA may also be used. PFDMA is combined with a free radical initiator 2,2'-azobis(2-methylpropionitrile) (AIBN) and the functionalized metal nanoparticles 220. A solvent such as cyclohexanone is added, and the mixture is heated until polymerization is completed (generally at least four hours). The presence of a solvent is necessary to overcome the common viscosity and wetting issues related to the high specific surface area of the functionalized metal nanoparticles 220; cyclohexanone may be used because it provides dissolution of heavily fluorinated monomers such as PFDMA, which allows the monomers to react with the functionalized metal nanoparticles 220 during polymerization. The resulting AlFA nanocomposite 230 is filtered, washed, and dried. In FIG. 2, m, x, and n refer to the number of each monomer unit contained in the brackets and may comprise the same or different number.

In another embodiment, the reactive nanocomposites according to the present invention may further comprise additional components such as metals metal oxides, complex inorganic oxidizers, and/or polyoxometallates, which are in addition to the reactive metal nanoparticles that are incorporated into the reactive nanocomposite via in-situ polymerization as described above in FIGS. 1-2. The metals may include, but are not limited to, Al, B, Mg, Si, Zr, Hf, Ni, Fe, W, Ta, and/or Ti, and mechanically mixed or alloyed powders including, but not limited to, alloys or mixtures of the elements previously described. The metal oxides may include, but are not limited to, $Bi_2O_3$, CuO, $Fe_2O_3$, $WO_3$, and $MoO_3$. The complex inorganic oxidizers or polyoxometallates may include, but are not limited to, $H_3[PMo_{12}O_{40}]$, $H_3[PW_{12}O_{40}]$ and $H_3[PSi_{12}O_{40}]$. The metals and/or metal oxides may comprise micron and/or nanoscale powders that are added to the reactive nanocomposites to improve or introduce additional reactivity by serving as an additional oxidizer and/or to increase density of the reactive nanocomposite. The metals and/or metal oxides may be incorporated into the reactive nanocomposite by functionalization and polymerization as described above. Alternatively, the metals and/or metal oxides may be mixed into a secondary resin or polymer and blended with the primary reactive nanocomposite using known methods.

In an alternative embodiment, the reactive nanocomposites may further comprise inorganic metal salts such as silver salts (e.g. $AgNO_3$, $AgIO_3$, etc.) and iodine salts (e.g. $I_2O_5$, etc.), as well as other salts such as quaternary ammonium salts and/or other suitable compounds and additives known in the art that are capable of neutralizing or eliminating a biological or chemical agent and/or disinfecting a surface or area. These salts and additives may be incorporated or mixed into the nanocomposite matrix in a similar manner to that described above with regard to the metals/metal oxides. Reactive nanocomposites containing the salts and/or other additives may then be applied to a surface or an environment that is known or suspected to contain a biological or chemical agent. The salts and additives may enhance the capability of biological or chemical agent neutralization through burning (as an incendiary), reacting to provide a toxic effect, or combinations thereof.

In a further embodiment, the reactive nanocomposites may comprise one or more energetic materials. These energetic materials may include, but are not limited to, high explosives (e.g. materials that detonate, which may include, but are not limited to, 1,3,5-trinitro-1,3,5-triazacyclohexane (RDX), octahydro-1,3,5,7-tetranitro-1,3,5,7-tetrazocine (HMX), trinitrotoluene (TNT), nitroglycerin (NG), nitroguanidine (NQ), 2,4-dinitroanisole (DNAN), and combinations thereof), propellants and pyrotechnics, (e.g. gunpowder, nitrocellulose-based powders, flash powders, composite propellants, etc.), and other suitable high burn-rate or explosive fluids, gels, powders, solids, and/or mixtures thereof. The energetic material must generally be one that is compatible with the reactive nanocomposite, meaning that incorporation of the reactive nanocomposite into the energetic material must not increase the sensitivity of the energetic material.

These energetic materials may be combined with the reactive nanocomposites using a variety of methods including dispersion by blending or mixing into a reactive nanocomposite powder using known methods; arrangement in layers such as in a laminate prepared from either compaction/compression or extrusion of the nanocomposite powder into one or more layers or the use of preformed films to serve as a layer or layers of the reactive laminate structure; and/or arrangement in concentric shells prepared from either compaction/compression or extrusion of the nanocomposite powder into one or more layers or the use of preformed films to serve as a layer or layers of the laminate structure or any other specific arrangement to improve reactivity or produce a desired energetic response. Alternatively, the reactive nanocomposites of the present invention may be incorporated directly into an existing explosive fill in order to enhance one or more aspects of the performance of the explosive fill. This incorporation into an existing energetic material such as an explosive fill may be accomplished via dispersion of the reactive nanocomposites by blending, mixing and/or adding a powdered or milled material comprising a reactive nanocomposite according to the present invention into the energetic material.

In another embodiment, the reactive nanocomposites may comprise an external structural shell. The external structural shell may comprise a variety of materials including, but not limited to, glass fiber composites, carbon fiber composites, aramid composites, metal laminates, solid metal (e.g. aluminum, steel, titanium), structural polymers (e.g. polycarbonate, polyamide, polyurethanes, Acetal, or other plastics), and other suitable materials or composites thereof. The structural shell is added (for example) to provide additional mechanical and/or blast controlling properties to the reactive nanocomposite, and/or to provide desired ballistic shapes and/or properties.

In an alternative embodiment, the reactive nanocomposites may be modified for use as a reactive ink or other media for use in printing and additive manufacturing technologies. These technologies may include, but are not limited to, layer-by-layer deposition of the reactive material that results in a three-dimensional object (e.g. three-dimensional printing), as well as printing of the reactive material into a two-dimensional pattern or architecture on a surface. The reactive nanocomposite may be modified by incorporating the nanocomposite material into a liquid such as a solvent or other carrier liquid to form a solution or suspension. Alternatively, the reactive nanocomposite may be heated above its melting point (with or without an additional liquid such as a solvent or other carrier liquid). In both cases, the solvent or other carrier liquid may optionally contain additives such as dyes and/or pigments. The reactive nanocomposite solution or suspension is then printed (two- and three-dimensional), sprayed, or otherwise deposited using any suitable known method onto a substrate to form one or more layers. Upon cooling of the reactive nanocomposite and/or evaporation of the solvent or other carrier liquid, the deposited reactive nanocomposite may comprise a reactive layer or liner that is removed from the substrate. Alternatively, the deposited reactive nanocomposite may comprise a coating or a desired pattern that remains on the substrate.

In an alternative embodiment, any of the reactive nanocomposites according to the present invention may also be combined with a thermosetting or thermoplastic resin or polymeric matrix to prepare a reactive structural nanocomposite. The reactive nanocomposite may be fabricated as shown in FIG. 2 as a powder and blended into one or more resins. Examples of suitable thermoplastic polymeric matrices may include poly(vinylidene fluoride), poly(hexafluoropropylene-co-vinylidene fluoride), and blends thereof. Examples of suitable thermosetting polymeric matrices may include one or more epoxy, urethane, bismaleimide, polyimide, or polyamide polymers or blends thereof. The polymeric matrix may provide improved mechanical, environmental, and/or chemical compatibility properties over the reactive nanocomposite alone. In addition, the thermosetting resin may impart improved processability to the material, a higher temperature capability, or both.

The following examples and methods are presented as illustrative of the present invention or methods of carrying out the invention, and are not restrictive or limiting of the scope of the invention in any manner.

Example 1

PAM-Co-Nano-Al Preparation

The following is an exemplary method of synthesizing PAM-co-nano-Al (nano-Al that is functionalized with PAM) substantially as depicted in FIG. 1. Aluminum nanoparticles (80 nm, 80% active Al content) (NovaCentrix, Inc.™) are stored under argon in a glove box ($O_2 \leq 1$ ppm; dew point=−80° C.) prior to use. PAM (Aldrich®) is used as received unless otherwise noted. PFDMA (SynQuest Laboratories, Inc.) is purified by vacuum distillation and stored under nitrogen in a refrigerator (4° C.) prior to use. Cyclohexanone is dried over $CaH_2$ and distilled prior to use in the polymerizations. AIBN (Aldrich®) is recrystallized from acetone prior to use.

A 1000 mL four-necked reaction vessel, fitted with an overhead stirrer, two rubber septa, and a glass stopper is charged with nano-Al powder (30.0 g, 1.11 mol) and hydroquinone (0.050 g, 0.45 mmol), which is added as a radical scavenger to prevent polymerization during the reaction. PAM (2.97 g, 12.5 mmol) is dissolved into 250 mL of cyclohexanone and transferred to the reaction vessel and stirred (235 rpm). A nitrogen atmosphere is established and maintained in the reaction vessel throughout the course of reaction. The vessel is then submerged into an external oil bath at 60° C., and the reaction is allowed to progress for 4 hours. The functionalized particles are isolated by vacuum filtration over a 0.2 μm PTFE membrane (Cole Parmer®) and washed with cyclohexanone and acetone to remove physisorbed PAM. The filtered product is then dried in a vacuum desiccator to remove residual solvent. Organic content of the PAM-co-nano-Al was determined to be about 4% by weight.

Example 2

AlFA Nanocomposite Preparation

The following is an exemplary method of synthesizing AlFA nanocomposites as depicted in FIG. 2. AlFA-X (X denotes the particle content in terms of particle wt %) nanocomposites were prepared by in-situ polymerization of PFDMA with varying concentrations of PAM-co-nano-Al as indicated in Table 1. A typical polymerization for the preparation of AlFA-30 is carried out using the following procedure, and this exemplary procedure may be used to prepare AlFA nanocomposites according to the present invention. A 1000 mL four-necked reaction vessel fitted with an overhead stirrer and three rubber septa is charged with PAM-co-nano-Al (15.0 g) and a free-radical initiator, AIBN (0.350 g, 2.13 mmol). The vessel is sealed and placed under a nitrogen atmosphere. PFDMA (35.0 g, 65.8 mmol) is added via a syringe to the reaction vessel followed by dry cyclohexanone (75 mL), which is transferred via cannula to serve as the solvent.

The reaction mixture is then subjected to three purge-freeze-pump-thaw cycles to remove dissolved oxygen. The reaction vessel, while under nitrogen purge, is immersed into a dewar containing liquid nitrogen. Once the reaction mixture is frozen, the reaction vessel is removed from the dewar, and the reaction mixture is allowed to thaw under vacuum. The reaction vessel is then re-immersed twice into the liquid nitrogen dewar, each time followed by nitrogen purge and thawing under vacuum for a total of three purge-freeze-pump-thaw cycles. After the final thaw is completed, the reaction vessel is placed under a blanket of nitrogen and then submerged into an external oil bath at 75° C. for a minimum of 4 hours. In most cases, polymerization was completed prior to 4 hours and could be observed by an increase in viscosity and precipitation of the nanocomposite from the solvent; however, the reaction was still held at temperature for 4 hours to ensure complete polymerization. After 4 hours, the heat is removed, and the reaction is allowed to cool to room temperature. The nanocomposite is removed from the reaction vessel, transferred to a filtration apparatus fitted with a 0.2 µm PTFE membrane, and washed with acetone to remove cyclohexanone and any unreacted monomer. The filtered product is then dried in a vacuum desiccator to remove residual solvent. Reaction yields between 90-95% were observed for each nanocomposite.

To ensure uniform distribution of the nano-Al throughout the material, the reactive nanocomposite is compounded for 3 minutes in a DACA Instruments benchtop twin-screw extruder at 150° C. The compounded material is then extruded through a circular die into a cylindrical clam-shell mold and allowed to cool to room temperature. The thermoplastic behavior of the poly(PFDMA) matrix allowed for successful compounding of all AlFA nanocomposites with the exception of the AlFA-70 nanocomposite. The AlFA-0 nanocomposite, which does not contain any nano-Al, was a white, waxy solid, while the other AlFA nanocomposites were gray, waxy solids with increasing metallic luster as nano-Al content increased.

TABLE 1

Reaction Conditions for the Synthesis of AlFA Nanocomposites

| Nanocomposite | PAM-co-nAl (g) | PFDMA (g) | AIBN (g) | Cyclohexanone (mL) |
|---|---|---|---|---|
| AlFA-0 | — | 50.0 | 0.50 | 75 |
| AlFA-10 | 5.0 | 45.0 | 0.45 | 75 |
| AlFA-30 | 15.0 | 35.0 | 0.35 | 75 |
| AlFA-50 | 25.0 | 25.0 | 0.25 | 75 |
| AlFA-60 | 30.0 | 20.0 | 0.20 | 75 |
| AlFA-70 | 35.0 | 15.0 | 0.15 | 75 |

Example 3

AlFA-50e Preparation

AlFA-50 was prepared as described above as a micron-scale powder. The powder was then blended with a structural bisphenol-F epoxy resin EPON 862® plus Epikure®-9553 or Epikure®-W to yield the reactive structural nanocomposite AlFA-50e.

Example 4

One-Pot Synthesis of AlFA-50

The following is an exemplary method of synthesizing AlFA-50 using a one-pot synthesis process. This exemplary procedure may be used to prepare AlFA nanocomposites according to the present invention. Aluminum nanoparticles (80 nm, 80% active Al content) (NovaCentrix, Inc.™) are used as received and are stored under argon in a glove box ($O_2 \leq 1$ ppm; dew point=−80° C.) prior to use. Prior to use, PFDMA (SynQuest Laboratories, Inc.) is washed with a 1M NaOH solution, rinsed with deionized water, dried with $MgSO_4$, filtered, and distilled under vacuum. PAM (Aldrich®) is used as received (a molecular weight of 238 g/mol is used for PAM due to the 25% diester content). AIBN (Aldrich®) is recrystallized from methanol or acetone prior to use. Cyclohexanone is dried over $CaH_2$ and distilled under nitrogen prior to use.

Aluminum nanoparticles (37.5 g) and AIBN (0.375 g) are transferred to the bottom half of a two-part, 1000 mL reaction vessel. A Teflon o-ring is placed on the reaction vessel along with the 4-neck top half of the reaction vessel, which is fitted with an overhead stirrer, vacuum tight bearing, and three rubber septa. The reaction vessel is sealed with a clamp to secure the top and bottom portions together. The reaction vessel is then purged with nitrogen to displace the air. PFDMA (23.4 mL) is added via a syringe to the reaction vessel through one of the rubber septa. PAM (2.08 g) is dissolved into the cyclohexanone (100 mL) and added via cannula to the reaction vessel. The overhead stirrer is turned on, and the mixture is stirred at 235 rpm for approximately 3 minutes.

The reaction vessel, while under nitrogen purge, is then immersed into a dewar containing liquid nitrogen. Once the reaction mixture is frozen, the reaction vessel is removed from the dewar, and the reaction mixture is allowed to thaw under vacuum. The reaction vessel is then re-immersed twice into the liquid nitrogen dewar, each time followed by nitrogen purge and thawing under vacuum for a total of three purge-freeze-pump-thaw cycles. After the final thaw is completed, the reaction vessel is placed under a blanket of nitrogen and then submerged into an external oil bath at 75° C. for a minimum of 4 hours with continuous stirring at 235 rpm. Once polymerization is complete, the heat is removed, and reaction vessel is allowed to cool to room temperature. The composite may then be removed from the reaction vessel and transferred to a filter with a 0.2 micron PTFE membrane, followed by washing with acetone under a reduced atmosphere to remove any residual solvent and/or monomer. The washed composite is transferred to a vacuum desiccator and allowed to sit overnight to remove any residual acetone or solvent. Typical yields for the one-pot synthesis method are around 95%. The final material may be used as is or milled down into a fine powder depending on processing requirements.

Example 5

Characterization of AlFA Nanocomposites

Materials and Methods

The following are methods employed to test the properties of PAM-co-nano-Al nanocomposites manufactured according to the present invention. Thermogravimetric analysis (TGA) is performed on a TA Instruments® SDT Q600 dual TGA/DTA. Nanocomposite samples (5 to 20 mg) are placed into a tared alumina crucible with an empty alumina crucible serving as the reference. All data is collected in dynamic mode under flowing argon (100 mL/min) from room temperature up to 800° C. at a rate of 5° C./min.

Differential Scanning calorimetry (DSC) is performed on a TA Instruments® Q1000 DSC. Samples (3-10 mg) are sealed in an aluminum pan with an empty aluminum pan serving as the reference. Each sample is subjected to a heat-cool-heat cycle to remove any stored thermal history in the material. After equilibrating at −90° C., samples are heated at 5° C./min to a final temperature of 150° C. Following the first heating cycle, the samples are cooled from 150° C. to −90° C. at a rate of 5° C./min and then subjected to a second heat ramp covering the same temperature range at 2° C./min. All reported data is collected during the final heating cycle.

Transmission electron microscopy (TEM) images are acquired on a Philips® CM200 microscope with $LaB_6$ emission source at an operating voltage of 200 keV. Microscope samples are prepared by embedding small slivers of the nanocomposites into flat molds filled with EMbed 812 resin and polymerized overnight in a 60° C. oven. The blocks are then ultramicrotomed with a PowerTome XL ultramicrotome by Boeckeler Instruments® and a 35° Diatome® diamond knife. Sections are cut at a thickness of 75 nm and a speed of 1 mm/sec. Ribbons of the sections are floated onto the water trough of the diamond knife and picked up and placed onto 3 mm 400-mesh hexagonal Cu grids and allowed to air dry. Once dry, the sections are ready to be imaged in the TEM.

Pellet combustion experiments are performed by placing an 8 mm long×4 mm diameter pellet of the respective nanocomposite onto a stainless steel wire mesh located in a vented fragmentation chamber under an air atmosphere. The pellets are initiated by a butane flame from directly below. A NAC Image Technology Memrecam® GX8 digital high speed video camera, collecting full frame, full color images at 3,000 frames per second, is used to record video of the pellet combustion experiments. Images from the high-speed video are subsequently analyzed using image processing software (IDL® 3.1, ITT Industries) in order to calculate intensity of reaction (light output) as a function of time.

X-ray powder diffraction (XRD) spectra are acquired on a Rigaku® DMAX B RU200 spectrometer using Cu $K_\alpha$ radiation. Identification of the observed patterns is accomplished by comparison with the ICDDS crystallographic database.

Quasi-static compression testing of 8 mm long×4 mm diameter right circular cylinders is carried out using an MTS-820 servo-hydraulic test frame, incorporating a self-aligning compression subpress (Wyoming Test Fixtures, model B-11) with precision-ground steel upper and lower platens. Testing is performed according to ASTM D695-10 under displacement control at a nominal strain rate of $10^{-3}$ $s^{-1}$. A digital video camera and associated image correlation software (Vic-Gauge 2.0, Correlated Solutions, Inc.) is used to record continuous strain data from multiple, redundant virtual strain gages during the testing. Simultaneous load data is obtained using a calibrated 10 kN load cell mounted on the load frame. Teflon® tape is used to lower the friction between the specimen end faces and both upper and lower loading platens, to minimize barreling. A minimum of two repeat specimens are tested for each AlFA composition.

TGA Analysis

Figure 3:
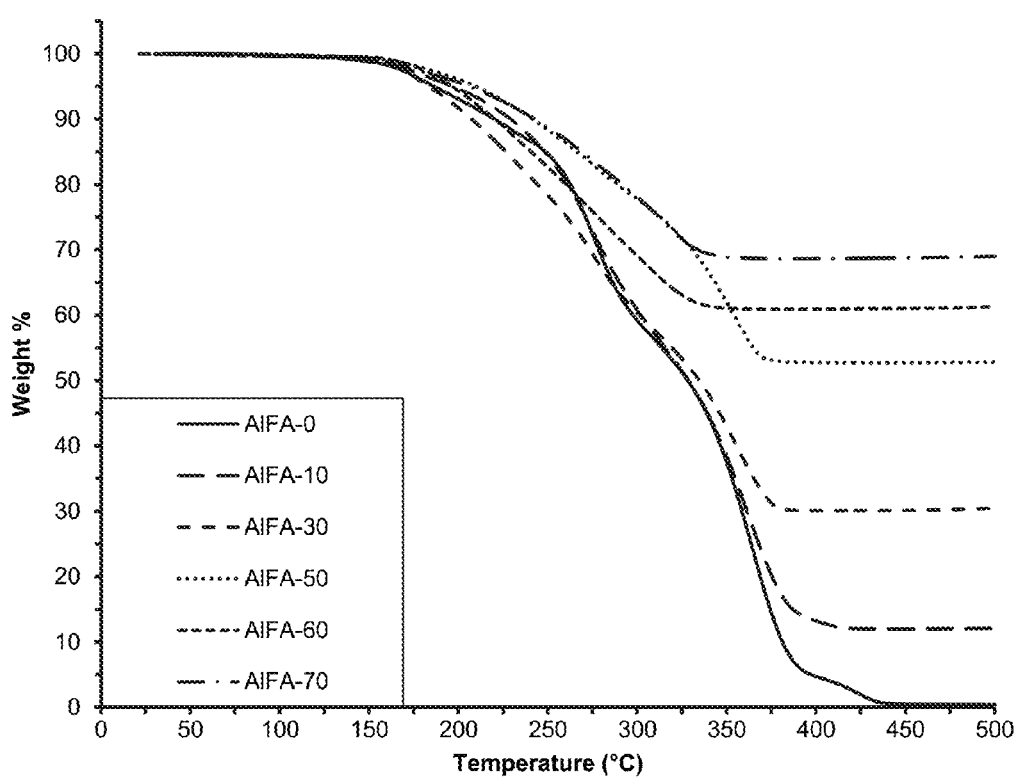
FIG. 3 is a graph depicting the thermogravimetric analysis (TGA) of several aluminized fluorinated acrylic ("AlFA") reactive nanocomposites.
Figure 4:
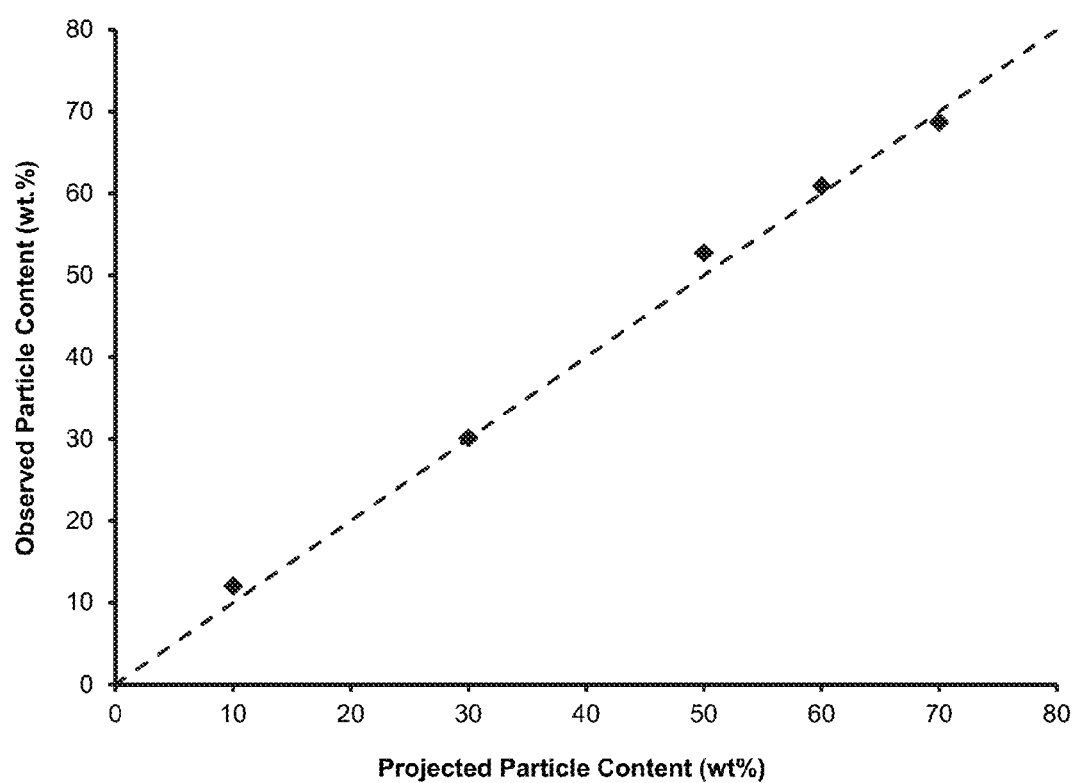
FIG. 4 is a graph depicting the relationship between the Projected Particle Content (weight %, X-axis) and the Observed Particle Content (weight %, Y-axis) obtained from the TGA analysis of FIG. 3.

FIGS. 3 and 4 contain the results of the TGA analysis. TGA analysis is performed to confirm the particle loading of the nanocomposite materials after compounding and extrusion. A noticeable weight loss is observed slightly above 150° C. associated with degradation of the polymer matrix, likely scission and decomposition of the perfluorinated alkyl tail to yield an alkene or alcohol. Complete degradation of the polymeric matrix is achieved by around 400° C. for each nanocomposite studied. The residual mass observed at 500° C. is used to determine the particle content of the nanocomposite.

FIG. 3 contains the TGA curves for of AlFA-0 (—) AlFA-10 (— —), AlFA-30 (— —), AlFA-50 ( . . . . . . ) AlFA-60 ( - - - ), and AlFA-70 (—.—) reactive nanocomposites, with Temperature (° C.) on the X-axis and Weight % on the Y-axis. FIG. 4 is a graph depicting the relationship between the Projected Particle Content (weight %, X-axis) and the Observed Particle Content (weight %, Y-axis) obtained from the TGA analysis shown in FIG. 3. The dotted line represents the Projected Particle Content, while the diamonds represent the actual Observed Particle Content for each AlFA nanocomposite. Based upon the TGA results, the in-situ polymerization approach utilized to prepare the AlFA nanocomposites allows for accurate control over the amount of particles that are directly incorporated into the polymer matrix.

DSC Analysis

DSC analysis is also performed on the AlFA nanocomposites to determine the melting temperature ($T_m$) as an indicator of the processability of the nanocomposite materials. The peak $T_m$ for the neat polymer (AlFA-0) is observed at 83.5° C.; increasing the particle content results in a slight increase in the melting temperature. The thermal analysis results obtained from both TGA and DSC are summarized in Table 2.

TABLE 2

Summary of the Thermal Analysis Data

| Nanocomposite | Wt. % | Vol. % | $T_m$ (° C.) |
|---|---|---|---|
| AlFA-0 | 0 | 0 | 83.5 |
| AlFA-10 | 12.0 | 7.47 | 84.5 |
| AlFA-30 | 30.1 | 20.3 | 85.5 |
| AlFA-50 | 52.7 | 39.8 | 84.0 |
| AlFA-60 | 60.9 | 48.0 | 87.0 |
| AlFA-70 | 68.7 | 56.5 | 85.5 |

Surprisingly, these materials do not display any significant loss in their thermoplastic behavior, even at high particle loadings. Because the nano-Al surface has been previously functionalized with a methacrylic monomer that is capable of reacting with the growing poly(PFDMA) chains during polymerization, it would be expected that the functionalized nano-Al would act as a crosslinker, as it has the potential to react with multiple propagating chains simultaneously due to the high surface coverage of monomer and the three-dimensional, spherical architecture of the particles. However, the thermal analysis data does not support this theory as there is not a significant increase (or decrease) in the $T_m$ or thermal stability (decomposition temperature) of the materials as would be expected for a highly crosslinked polymer.

TEM Imaging

Figure 5:
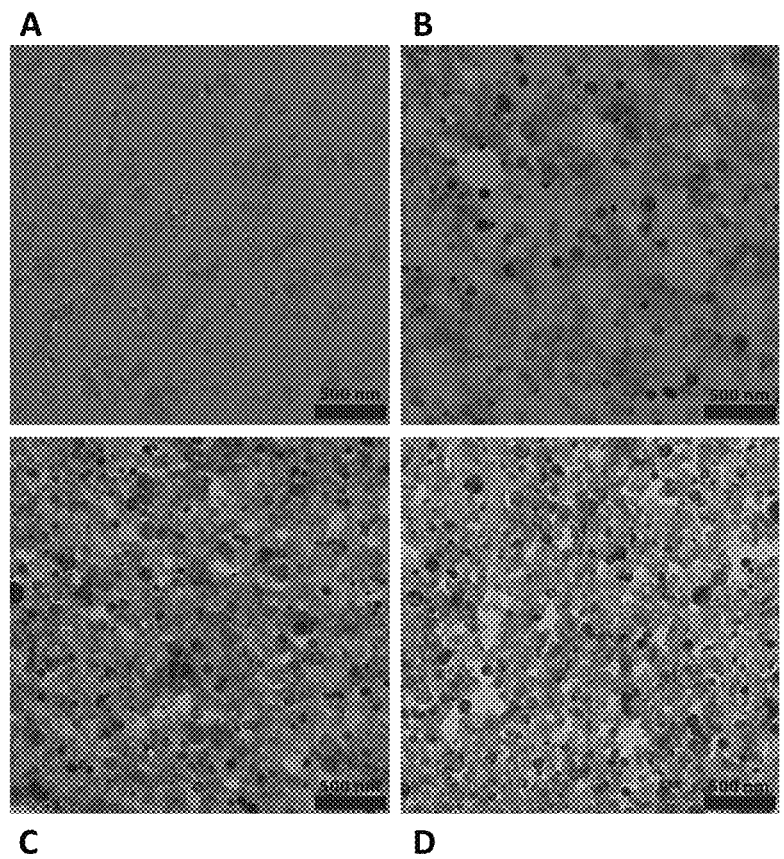
FIGS. 5A-D are transmission electron microscopy images of AlFA-10, AlFA-30, AlFA-50, and AlFA-60 nanocomposites.

Both the mechanical properties and reactivity of the nanocomposites are dependent on the interface between the polymer matrix and the nano-Al filler. TEM specimens of each nanocomposite are prepared in order to characterize the particle-polymer interface and microstructure as a function of particle content. FIG. 5 contains TEM images of (A) AlFA-10; (B) AlFA-30; (C) AlFA-50; and (D) AlFA-60 in the extruded form. In nanocomposites made according to the present invention, reactivity is derived from the interaction (reaction) of the nano-Al with fluorine atoms found within the polymer matrix as described in Equation 1 above; thus, increasing intimacy between the two components should increase the reactivity of the material. Additionally, stress transfer from the polymer matrix into the nano-Al filler also requires an intimate chemical and/or mechanical interaction between the two. Intimate and near-uniform mixing of particles with the polymer matrix after compounding and extrusion is evident from the micrographs, the initial agglomeration of the as-received particles notwithstanding. There are no visible signs of particle-matrix decohesion, suggesting that the interface is continuous and that the PAM layer on the oxide surface has become integrated within the polymer matrix.

The AlFA-10 and AlFA-30 nanocomposites, FIGS. 5A and 5B, respectively display small areas of aggregation, but for the most part, the particles appear to be homogeneously dispersed throughout the matrix. Moreover, there appear to be few voids present within the samples; a proportion of the voids that are observed in FIGS. 5A and 5B are considered artifacts from TEM sample preparation, such as particle pull-out or matrix tearing during microtomy. Aggregation is present in the consolidated AlFA-50 and AlFA-60 nanocomposites in FIGS. 5C and 5D, respectively; however, it is difficult to distinguish from the matrix due to the high particle loadings. The amount of porosity in the nanocomposite materials also increases with the higher particle loadings. FIGS. 5C and 5D show voids within the aggregates that were not penetrated by monomer or polymer during polymerization or compounding and extrusion.

Figure 6:
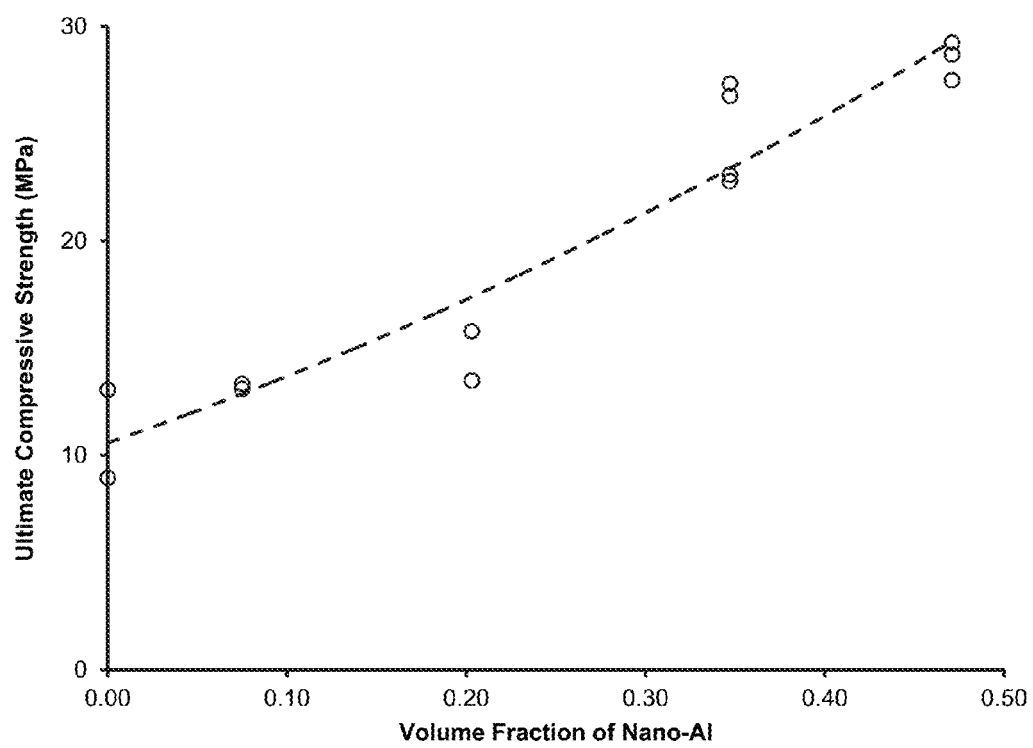
FIG. 6 is a plot showing measured ultimate compressive stress as a function of nano-Al content.

FIG. 6 is a plot showing measured ultimate compressive strength (MPa, Y-axis) as a function of nano-Al content (Volume Fraction, X-axis). The neat polymer (AlFA-0) displays a peak compressive strength of around 11 MPa. As expected, the addition of PAM functionalized particles into the polymer matrix results in an increase in compressive strength, with the highest values, about 25-28 MPa, obtained for the AlFA-50 and 60 nanocomposites. The increase in compressive strength is likely due to the high particle loadings and also the direct chemical bonding between the nano-Al and the polymer matrix.

Pellet Combustion Experiments and XRD Analysis

For the combustion experiments, an AlFA nanocomposite series is prepared with particle content varying from 10 to 70 wt % nano-Al. With the exception of the AlFA-70 composition, all materials are consolidated by hot extrusion, followed by machining into cylindrical pellets that are approximately 8 mm long and 4 mm in diameter. Semi-quantitative combustion rate experiments are performed by igniting each composition with a small butane flame and allowing the pellets to burn open to lab air. The combustion events are recorded with a digital high speed color video camera operating at 3,000 frames per second.

Figure 7:
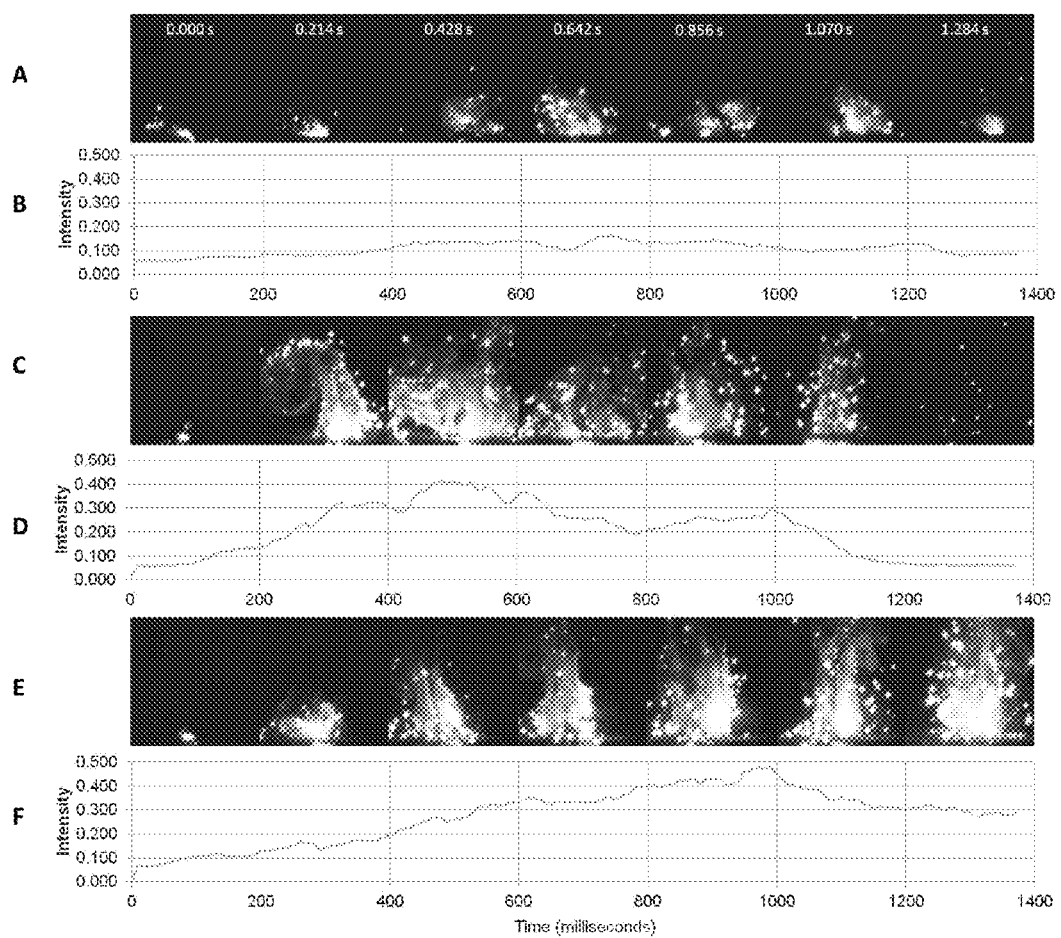
FIGS. 7A-F are a series of time-sequence images obtained from the combustion of AlFA-30, AlFA-50, and AlFA-60 nanocomposites and a series of corresponding graphs depicting the evolution of the measured intensity of the combustion of the respective reactive nanocomposites.
Figure 8:
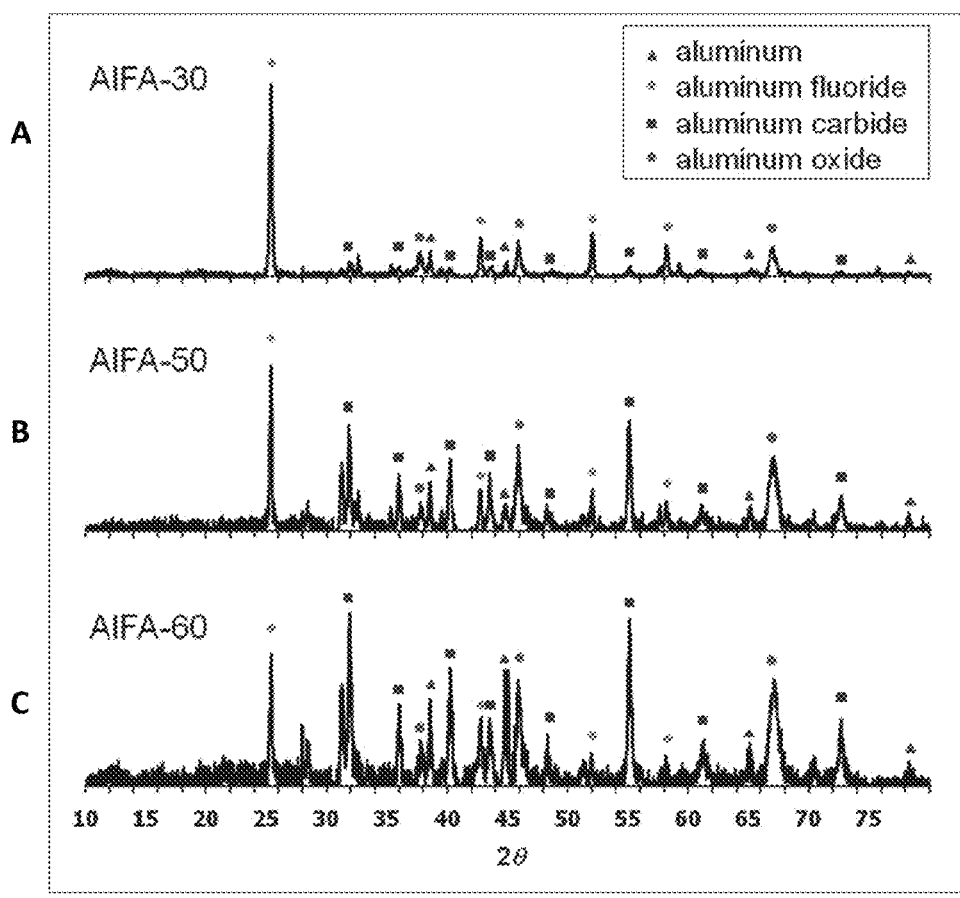
FIGS. 8A-C show the x-ray powder diffraction analysis of the solid products produced for each respective combustion experiment in FIGS. 7A-F for AlFA-30, AlFA-50, and AlFA-60 nanocomposites.

FIG. 7 is a time-sequence of full color images obtained from the combustion of (A) AlFA-30; (C) AlFA-50; and (E) AlFA-60 materials, accompanied by corresponding graphs showing the evolution of the measured intensity of the video images as a function of time for each respective nanocomposite (B) AlFA-30; (D) AlFA-50; and (F) AlFA-60 materials. FIG. 8 shows the XRD analysis of the solid products produced for each respective combustion experiment in FIG. 7: (A) AlFA-30; (B) AlFA-50; and (C) AlFA-60.

All of the nanocomposites, with the exception of AlFA-0 and AlFA-10 (data not shown), demonstrate a self-sustaining deflagration upon ignition. Since the AlFA-0 nanocomposite did not contain any nano-Al, the pellet simply melts upon heating. The AlFA-10 nanocomposite also initially melts but subsequently ignites after sustained heating due to the loss of polymer—as smoke and char—until the nano-Al becomes concentrated enough to sustain a reaction.

In contrast, ignition of the AlFA-30 pellet as shown in FIGS. 7A-B occurs immediately upon contact with the flame. A self-sustaining intense white-yellow flame is observed, accompanied by the production of a significant amount of smoke and black char. The char is collected and analyzed by XRD in FIG. 8A to determine the identity of the solid products. The primary component of the char is $AlF_3$, indicating that nano-Al is indeed reacting with the fluorinated polymer matrix in a similar manner to PTFE. Other products also present in the char include aluminum oxide, unreacted metallic aluminum (presumably ejected during the rapid burning), aluminum carbide ($Al_4C_3$), and aluminum oxide carbide, although the latter two products are minor compared to $AlF_3$.

Combustion of the AlFA-50 pellet in FIG. 7C yields the most intense and rapid reaction, as compared to the other nanocomposite compositions. The pellet ignites readily upon exposure to the butane flame, producing an intense yellow-orange flame that rapidly consumes the entire pellet and releases smoke and gasses that physically moved the pellet across the wire gauze as it burned. The intensity plot in FIG. 7D shows two distinct peaks, one around 500 milliseconds and another around 1.0 second, with the deflagration process requiring around 1.3 seconds for complete combustion. The char obtained as a product of the reaction is black and gray in color. XRD analysis in FIG. 8B again confirms the presence of $AlF_3$ as the major product, but the $Al_4C_3$ and aluminum oxide peaks were more prevalent than is observed for the AlFA-30 char in FIG. 8A. Residual aluminum and aluminum oxide carbide are also present but only as trace phases.

Ignition and deflagration of the AlFA-60 pellet as shown in FIGS. 7E-F is slower than the AlFA-50 pellet in FIG. 7C. A similar yellow-orange flame is produced, which steadily grows in intensity as the reaction progresses. A total reaction time of more than 1.5 seconds is required to obtain complete combustion of the pellet, with the most intense flames appearing about 1.0 second after ignition. The char product is primarily a dark grey color. XRD analysis in FIG. 8C confirms $Al_4C_3$ as the major component of the char, followed by $AlF_3$ and aluminum oxide; residual aluminum is also present as a trace phase.

The stoichiometric reaction between nano-Al and PTFE resulting in $AlF_3$ and carbon (as previously shown in Equation 1) requires a composition equivalent to 26.5% Al and 73.5% PTFE by weight as shown in Equation 2.

$$26.5\% \text{ Al} + 73.5\% (-CF_2-)_n \rightarrow 82.4\% \text{ AlF}_3 + 17.6\% \text{ C} \quad (2)$$

TGA oxidation studies confirmed that the nano-Al used in the AlFA nanocomposites has an 80% active aluminum content due to the presence of an inert oxide shell; therefore, 20% of the nano-Al mass does not contribute anything to the reaction. Moreover, the poly(PFDMA) fluoropolymer contains about 60% fluorine by mass, compared to 75% for PTFE. Adjusting the stoichiometry of Equation 2 to account for both these factors results in a stoichiometric composition for complete fluorination equivalent to 26.5% nano-Al in 73.5% poly(PFDMA) fluoropolymer by weight as shown in Equation 3.

$$26.5\% \text{ nano-Al} + 73.5\% \text{poly(PFDMA)} \rightarrow 78.0\% \text{ AlF}_3 + 16.70\% \text{C} + 5.3\% \text{Al}_2\text{O}_3 \quad (3)$$

The preceding analysis provides a thermodynamic basis for $AlF_3$ being the dominant product in the soot collected from the AlFA-30 combustion, since the AlFA-30 composition is very close to the stoichiometric condition required for complete fluorination. Moreover, AlFA-30 being slightly fuel rich leaves a small residual amount of aluminum available to react with oxygen and/or carbon to yield the observed oxide and/or carbide products (Equations 4 and 5), respectively.

$$4Al + 3O_2 \rightarrow 2Al_2O_3 \; \Delta H^\circ = -3351.44 \text{ kJ} \quad (4)$$

$$4Al + 3C \rightarrow Al_4C_3 \; \Delta H^\circ = -205.99 \text{ kJ} \quad (5)$$

Because the open burn testing was carried out in air, it is possible that both oxidation and fluorination mechanisms can make contributions towards the overall energetic performance of the material; therefore, it is possible to optimize the material for both reactions by combining Equations 1 and 4 as shown below in Equation 6. Once again accounting for the active aluminum and fluorine available in nano-Al and poly (PFDMA), respectively, Equation 6 can be easily translated into Equation 7.

$$6Al+3(—CF_2—)_n+3O_2 \rightarrow 2Al_2O_3+2AlF_3+3C \; \Delta H^0=-3943.42 \text{ kJ} \quad (6)$$

$$41.7\% \text{nano-Al}+38.6\% \text{poly(PFDMA)}+19.7\%O_2 \rightarrow 48.6\% Al_2O_3+42.4\% AlF_3+9.0\%C \quad (7)$$

Examination of Equation 7 indicates that a composition equivalent to 51.9% nano-Al and 48.1% poly(PFDMA) by weight is required for optimization of both fluorination and oxidation. The AlFA-50 composition is close to this stoichiometric composition, and it was also the most reactive nanocomposite in combustion tests, requiring the shortest overall time to achieve complete deflagration and producing the most intense overall flame (see FIGS. 7C and D). The increased performance of the AlFA-50 nanocomposite, as compared to the other AlFA nanocomposites, is likely due to its proximity to near stoichiometric conditions. Enough aluminum was present in the nanocomposite to support simultaneous oxidation and fluorination. The large plume present during combustion of the AlFA-50 nanocomposite suggests that aluminum is being ejected from the pellet and is reacting in air accompanied by the combustion of the carbonaceous byproducts from the polymer and the carbon produced during fluorination (see FIGS. 7C and D). These events provide additional heat to the system thereby enhancing the overall burn rate for that composition. The heat further accelerates diffusion between the reacting species, thereby increasing the rate of reaction. Additionally, the adiabatic flame temperature for oxidation of aluminum is approximately 550° C. hotter than the adiabatic flame temperature for fluorination, therefore one would expect the AlFA-50 combustion to occur faster than the pure fluorination observed in the AlFA-30 composition because the higher temperatures produced during combustion will enhance the overall rate of reaction.

The AlFA-60 nanocomposite generally takes longer to react because more aluminum is consumed through air oxidation and carbide formation due to the lack of fluorine present in the composition. These reactions are kinetically slower than fluorination and formation of the carbide, although exothermic, produces much less heat than combustion of the carbonaceous byproducts. Therefore, less heat is produced to enhance the overall burn rate and a slower burn time is observed, which is consistent with the intensity profiles shown in FIG. 7; the AlFA-60 data shows no peak around 500 milliseconds, corresponding with the fluorination event that was seen for the AlFA-30 and AlFA-50 material (see FIGS. 7E and F). However, the peak corresponding to oxidation (1.0 seconds) is still present.

Furthermore, an additional amount of energy equivalent to a maximum of −1180.50 kJ can be released by combustion of the carbon produced as a byproduct of the fluorination event. A significant increase in the formation of $Al_4C_3$ was observed in the AlFA-60 nanocomposite compared to the others, although some $Al_4C_3$ was present in the AlFA-50 soot (see FIG. 8B). The mechanism(s) for carbide formation are still unclear as carbide can be produced either through reaction of the aluminum with carbon, Equation 5, or aluminum oxide with carbon, Equation 8; however, reaction with residual aluminum is thermodynamically preferred.

$$2Al_2O_3+3C \rightarrow Al_4C_3+3O_2 \; \Delta H^0=+3145.5 \text{ kJ} \quad (8)$$

The carbon required to produce the carbide must come from the polymer, either in the methacrylate backbone or from carbon produced during fluorination. In the AlFA-60 nanocomposite, specifically, the composition is fuel-rich with more than enough aluminum present to support fluorination and oxidation as well as carburization. If it is assumed that the carbon produced from fluorination is also responsible for carbide formation, then Equation 9 is obtained which is readily translated into Equation 10 after accounting for the active aluminum in nano-Al and available fluorine in poly (PFDMA).

$$10Al+3(—CF_2—)_n+3O_2 \rightarrow 2Al_2O_3+2AlF_3+Al_4C_3 \; \Delta H^0=-4149.41 \text{ kJ} \quad (9)$$

$$54.3\% \text{nano-Al}+30.2\% \text{poly(PFDMA)}+15.5\%O_2 \rightarrow 37.2\% AlF_3+33.8\% Al_2O_3+29.0\% Al_4C_3 \quad (10)$$

This corresponds to a composition of 64.3% nano-Al and 35.7% poly(PFDMA) which is near the AlFA-60 composition tested. Notably, the formation of an $Al_4C_3$ phase (($\Delta H_F(Al_4C_3)=-205.99$ kJ/mol) does not contribute significantly to the overall energetic release, since it provides only −1.88 kJ per gram of aluminum.

Deviations towards fuel-lean compositions result in loss of reactivity as was observed by the lack of reaction for the AlFA-10 nanocomposite. Particle contents closer to the stoichiometric conditions for fluorination yet slightly fuel rich, such as the AlFA-30 nanocomposite, resulted in near complete reaction between the nano-Al and the fluorinated matrix, with only minor phases present in the reaction products indicating both air oxidation and/or carbide formation. Because these reactions occurred in the presence of air, the prevalence of $AlF_3$ as the dominant product of AlFA-30 combustion suggests that fluorination is kinetically favored over oxidation even though formation of the oxide is thermodynamically preferred. However, as the composition is adjusted to fuel-rich conditions—AlFA-50 and AlFA-60—the oxide and carbide products grow rapidly accompanied by a decrease in $AlF_3$. These compositions are fluorine deficient, and therefore, air oxidation (Equation 4) can compete with fluorination (Equation 3) and eventually becomes the dominant mechanism for aluminum consumption after the all of the fluorine has been consumed. This conclusion is supported by the intensity profiles found in FIG. 7. The first peak in the AlFA-50 data is likely due to the kinetically faster fluorination reaction (or a combination of fluorination and oxidation), and the second peak (around 1.0 seconds) is likely due solely to the oxidation of the remaining aluminum, with both reactions contributing towards the overall intensity. Moreover, if carbide is formed as a product from the reaction of nano-Al with carbon produced during the initial fluorination (Equation 5), then this explains why the carbide phase is only present in the fuel-rich mixtures as fluorination is kinetically preferred and completely consumes the aluminum under near stoichiometric conditions for fluorination (AlFA-30), leaving no aluminum available to react with the carbon.

Figure 9:
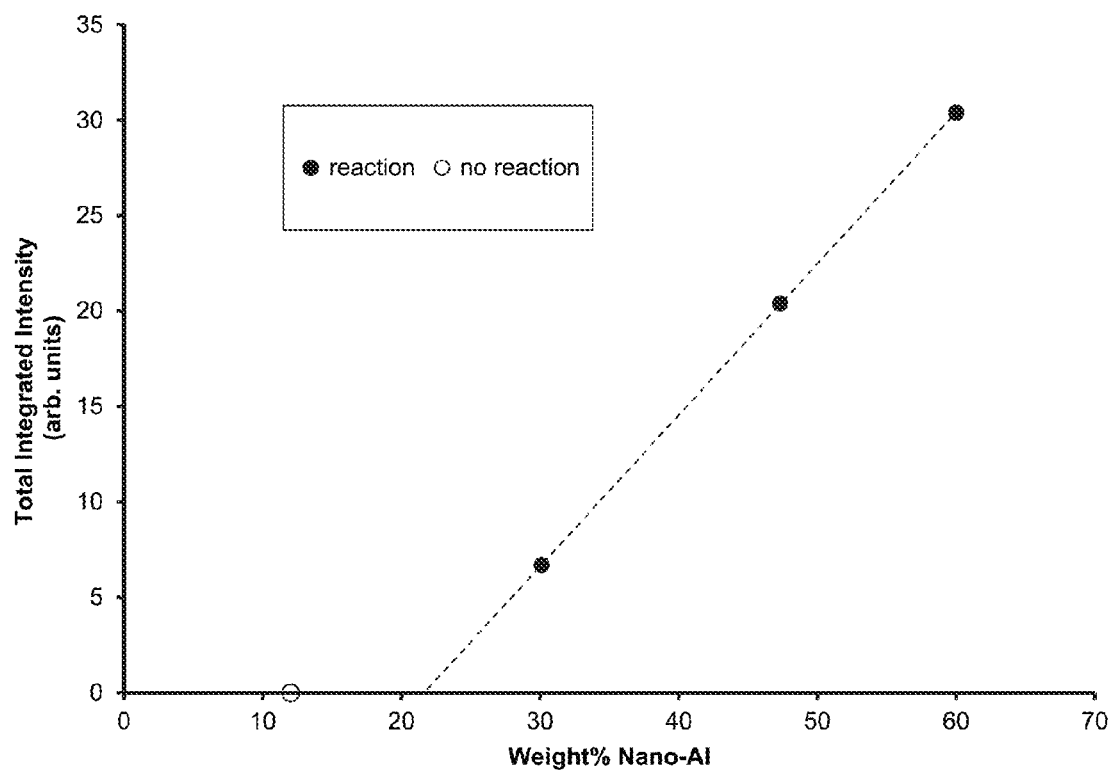
FIG. 9 is a plot of the amount of nano-Al present versus the total integrated intensity.

By numerically integrating the total area under the intensity-time curves from FIG. 7, one may obtain a simple, semi-quantitative measure of the extent of reaction. When this integration is done, it shows that the total integrated intensity scales linearly with the amount of nano-Al present in the nanocomposite. FIG. 9 is a plot of the amount of nano-Al present (wt %, X-axis) versus the total integrated intensity (arbitrary units, Y-axis). The intercept on the horizontal axis is around 22 wt % nano-Al, which tends to indicate that this amount is a minimum nano-Al content for self-sustained combustion reaction under a specific set of experimental conditions. That the AlFA-10 composition (12.0 wt % nano-Al) did not achieve a self-sustaining reaction is consistent with this theory (data no shown).

Figure 10:
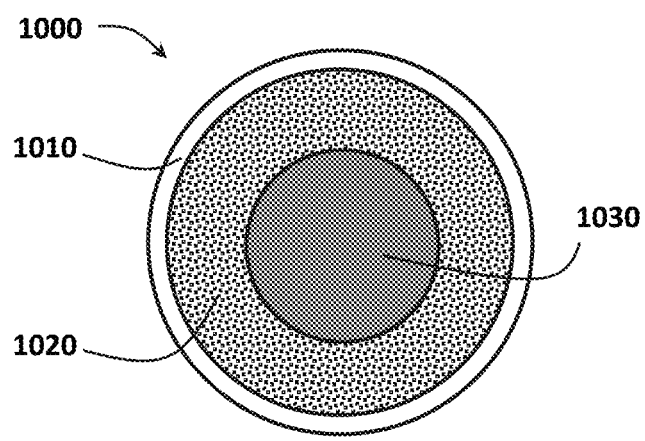
FIG. 10 is a cross-sectional view of an infiltrated open cell metal foam with an external structural shell and a filled core.

The present invention further includes reactive nanocomposite foams comprising any of the reactive nanocomposites according to the present invention that are extruded and infiltrated into an open cell foam. FIG. 10 is a cross-sectional view of an exemplary reactive nanocomposite foam 1000 comprising an open cell foam 1020 infiltrated with a reactive nanocomposite (not separately labeled). The open cell foam 1020 may be metallic or non-metallic (e.g. metal oxide, carbon, vitreous carbon, SiC, graphite, polyurethane, etc.). Examples of metal foams may include aluminum and aluminum alloys, as well as nickel, iron, copper, titanium, lead, tungsten, and molybdenum and other suitable metals or alloys thereof. The open cell foam 1020 may be added for structural support and/or as additional reactive or blast-enhancing material, or for fragmenting purposes or combinations thereof. Open cell foams 1020 are characterized by a large number of open pores formed by an interconnected network of material and may comprise a variety of shapes ranging from a flat sheet to a cylindrical tube as depicted in FIG. 10. The pores may range in size from microns to millimeters in diameter.

As previously described, a ligand is dissolved in a solvent and mixed with reactive metal nanoparticles to form functionalized reactive metal nanoparticles. An optional free radical scavenger may be used. The functionalized reactive metal nanoparticles are mixed with a free-radical initiator and at least one fluorinated monomer and mixed at an elevated temperature to produce a reactive nanocomposite. The open cell foam 1020 may then be placed in a mold or other device described above such as a simple cavity, with or without a mandrel, or a die. The reactive nanocomposite (with or without a thermosetting or thermoplastic resin) is extruded into the mold such that the reactive nanocomposite infiltrates the open cell foam 1020 and fills at least a portion of the pores.

In the embodiment depicted in FIG. 10, the reactive nanocomposite foam 1000 further comprises an external structural shell 1010. The external structural shell 1010 may comprise a variety of materials including, but not limited to, glass fiber composites, carbon fiber composites, aramid composites, metal laminates, solid metal (e.g. aluminum, steel, titanium), structural polymers (e.g. polycarbonate, polyamide, Acetal, or other plastics), and other suitable materials or composites thereof. The external structural shell 1010 may be added (for example) to provide additional mechanical and/or blast controlling properties to the reactive nanocomposite foam.

In one embodiment, the reactive nanocomposite foam 1000 may comprise a hollow core. In an alternative embodiment such as the one depicted in FIG. 10, the core may be filled with an explosive 1030. In other embodiments, the core may be filled with a variety of materials including, but not limited to, one or more explosives, pyrotechnic materials, and/or a dense metallic or non-metallic blast-enhancing, fragmentation-enhancing, and/or mechanical shear-inducing material, and/or combinations thereof. The explosive(s) may comprise any suitable explosive known in the art, including solid or liquid; ideal or non-ideal; metalized or non-metalized; and/or composite explosives. Examples of suitable explosives may include but are not limited to, 1,3,5-trinitro-1,3,5-triazacyclohexane (RDX), octahydro-1,3,5,7-tetranitro-1,3,5,7-tetrazocine (HMX), trinitrotoluene (TNT), nitroglycerin (NG), nitroguanidine (NQ), 2,4-dinitroanisole (DNAN) and combinations thereof). Examples of dense metallic fragments may include steel or tungsten spheres, hexagons or cubes. Examples of mechanical shear-inducing materials may include steel or tungsten shot ("BBs").

The reactive liner, coating, sleeve, or insert may be manufacturing using a printing technique according to the present invention. Such reactive structures may be used to control fragmentation, blast effects, etc.

Example 5

Reactive Nanocomposite Foam Preparation

A 40 pores per inch (ppi) open cell aluminum foam (ERG Duocel) is placed into a copper clamshell mold and attached to a benchtop extruder. An AlFA-50-PFDMA (50 wt %) nanocomposite according to the present invention is introduced to the extruder after the mold equilibrates to 160° C. The nanocomposite is compounded for three minutes before being extruded through a die and into the mold. The nanocomposite material is allowed to flow into the mold until it began to flow out of the vent, at which time the flow is shut off. The mold is then removed from the die and allowed to cool. After cooling, the mold is opened, and the infiltrated foam is removed.

The present invention further includes methods of using any of the reactive nanocomposite(s) and/or reactive nanocomposite foam(s) herein described. The method comprises forming the reactive nanocomposite and/or reactive nanocomposite foam into a reactive nanocomposite structure having a desired shape, including, but not limited to, reactive liners or coatings, casings such as munitions casings, sleeves, inserts, cylinders, shape charges, rods, and foams, including both metallic and non-metallic foams. The reactive liner, coating, casing, sleeve, or insert may be manufacturing using a printing technique according to the present invention. In one embodiment, the reactive liner is filled with one or more materials including, but not limited to, explosives, pyrotechnic, or pyrophoric materials; a dense metallic or non-metallic blast-enhancing, fragmentation-enhancing, and/or mechanical shear-inducing material; and/or combinations thereof. The explosive(s) may comprise any suitable explosive known in the art, including solid or liquid; ideal or non-ideal; metalized or non-metalized; and/or composite explosives. Examples of suitable explosives may include but are not limited to, 1,3,5-trinitro-1,3,5-triazacyclohexane (RDX), octahydro-1,3,5,7-tetranitro-1,3,5,7-tetrazocine (HMX), trinitrotoluene (TNT), nitroglycerin (NG), nitroguanidine (NQ), 2,4-dinitroanisole (DNAN), and combinations thereof). Examples of dense metallic fragments may include steel or tungsten spheres, hexagons or cubes. Examples of mechanical shear-inducing materials may include steel or tungsten shot ("BBs").

In an alternative embodiment, the method further comprises initiating the reactive nanocomposite and/or reactive nanocomposite foam using at least one of friction, impact, electrical discharge, heat/temperature flux, mechanical shock, explosion, and detonation.

Although this invention has been described with respect to certain preferred embodiments, various other embodiments and various changes and modifications to the disclosed embodiment(s) will become apparent to those skilled in the art. All such other embodiments, changes, and modifications are intended to come within the spirit and scope of the appended claims.

What is claimed is:

1. A method of making a reactive nanocomposite, the method comprising:
dissolving a ligand in a solvent;
adding the ligand solution to a mixture comprising a plurality of first reactive metal nanoparticles and a free radical scavenger;

stirring the mixture with the ligand solution at a first elevated temperature to produce functionalized reactive metal nanoparticles having the ligand coupled to an exterior surface of first reactive metal nanoparticles of the plurality; and mixing the functionalized reactive metal nanoparticles with a free-radical initiator, a fluorinated monomer, and additional solvent at a second elevated temperature, such that the ligand interacts with the fluorinated monomer, thereby incorporating the functionalized metal nanoparticles into a fluorinated polymer matrix by in-situ polymerization.

2. The method of claim 1, wherein the first reactive metal nanoparticles of the plurality comprising at least one selected from the group consisting of of Al, B, Mg, Si, Zr, Hf, Fe, and Ti.

3. The method of claim 1, wherein the ligand is at least one selected from the group consisting of (3-methacryloxypropyl)trimethoxysilane, 2-carboxyethylacrylate, and phosphoric acid 2-hydroxyethyl methacrylate ester.

4. The method of claim 1, wherein the fluorinated polymer matrix comprises a fluorinated acrylate polymer.

5. The method of claim 1, wherein the fluorinated polymer matrix is at least one selected from the group consisting of poly(1H,1H,2H,2H-perfluorodecyl methacrylate), poly(vinylidene fluoride), and poly(hexafluoropropylene-co-vinylidene fluoride).

6. The method of claim 1, further comprising:
milling the reactive nanocomposite to form a reactive powder.

7. The method of claim 1, further comprising:
incorporating a plurality of additional oxidizer particles into the reactive nanocomposite, the additional oxidizer particles of the plurality comprising at least one selected from the group consisting of a second reactive metal particle, a metal oxide, a complex inorganic oxide, and a polyoxometallate.

8. The method of claim 1, further comprising:
incorporating a silver salt, an iodine salt, a quaternary ammonium salt, or a combination thereof into the reactive nanocomposite.

9. The method of forming a reactive laminate, the method comprising:
forming a first layer comprising the reactive nanocomposite of claim 1;
forming a second layer comprising an energetic material; and
coupling the first layer to the second layer.

10. The method of claim 1, further comprising:
enclosing the reactive nanocomposite in an external structural shell, comprising at least one selected from the group consisting of a glass fiber composite, a carbon fiber composite, an aramid composite, a monolithic metal, a metal laminate, and a structural polymeric matrix.

11. The method of claim 1, further comprising:
combining the reactive nanocomposite with a thermosetting polymer matrix, a thermoplastic polymer matrix, or both.

12. A method of using the reactive nanocomposite of claim 1 comprising:
forming the reactive nanocomposite into a reactive nanocomposite structure comprising at least one selected from the group consisting of a liner, a coating, a casing, a sleeve, an insert, a cylinder, a shape charge, a rod, and an open cell foam.

13. The method of claim 12, further comprising:
filling the reactive nanocomposite structure with at least one selected from a group consisting of an explosive material, a pyrotechnic material, a pyrophoric material, a blast-enhancing material, a fragmentation-enhancing material, and a mechanical shear-inducing material.

14. A printing method comprising:
modifying the reactive nanocomposite of claim 1 to form a reactive nanocomposite fluid, wherein modifying the reactive nanocomposite comprises at least one selected from the group consisting of suspending the reactive nanocomposite in a carrier liquid, dissolving the reactive nanocomposite in a solvent, and heating above a melting point of the reactive nanocomposite; and
depositing a layer of the reactive nanocomposite fluid onto a substrate surface.

15. The method of claim 14, wherein the reactive nanocomposite fluid further comprises: a pigment or a dye.

16. The method of claim 14, wherein depositing the reactive nanocomposite further comprises a three-dimensional printing method.

17. The method of claim 14, further comprising:
depositing a plurality of layers of the reactive nanocomposite fluid onto the surface of the substrate to create a reactive liner.

18. A method of making a reactive nanocomposite foam comprising:
providing the reactive nanocomposite of claim 1;
providing an open cell foam defining a core and a plurality of pores;
placing the open cell foam into a mold; and
processing the reactive nanocomposite with the mold such that the reactive nanocomposite infiltrates the open cell foam to fill at least a portion of the pores.

19. The method of claim 18, further comprising:
filling the core of the open cell foam with at least one selected from the group consisting of an explosive material, a pyrotechnic material, a pyrophoric material, a blast-enhancing material, a fragmentation-enhancing material, and a mechanical shear-inducing material.

20. A method of claim 18, wherein the mold has a shape selected from the group consisting of a liner, a coating, a casing, a sleeve, an insert, a cylinder, a shape charge, a rod, and a foam.

21. The method of claim 20, further comprising:
filling the reactive nanocomposite foam structure with at least one selected from the group consisting of an explosive material, a pyrotechnic material, a pyrophoric material, a blast-enhancing material, a fragmentation-enhancing material, and a mechanical shear-inducing material.

* * * * *